(12) United States Patent
Noble et al.

(10) Patent No.: US 8,845,870 B2
(45) Date of Patent: Sep. 30, 2014

(54) DIGITAL POTENTIOSTAT CIRCUIT AND SYSTEM

(75) Inventors: Bradley L. Noble, Edwardsville, IL (US); Michael J. Shaw, Edwardsville, IL (US)

(73) Assignee: Board of Trustees of Southern Illinois University, Edwardsville, IL (US)

( * ) Notice: Subject to any disclaimer, the term of this patent is extended or adjusted under 35 U.S.C. 154(b) by 413 days.

(21) Appl. No.: 13/371,230

(22) Filed: Feb. 10, 2012

(65) Prior Publication Data

US 2012/0205258 A1 Aug. 16, 2012

Related U.S. Application Data

(60) Provisional application No. 61/441,737, filed on Feb. 11, 2011.

(51) Int. Cl.
  *G01N 27/327* (2006.01)
  *G01N 27/49* (2006.01)
  *G01N 27/48* (2006.01)

(52) U.S. Cl.
  CPC .................................. *G01N 27/48* (2013.01)
  USPC ............... 204/406; 204/403.01; 204/412

(58) Field of Classification Search
  CPC .............. G01N 27/4065; G01N 27/48; G01N 27/4166; G01N 27/403; G01N 27/416; G01N 27/49; G01N 27/28; G01N 27/3273; G01N 27/4161; C02F 1/46104
  USPC ............. 204/406, 229.4–229.9, 230.6–230.8; 324/425, 71.1, 71.2
  See application file for complete search history.

(56) References Cited

U.S. PATENT DOCUMENTS

| 2005/0158787 A1* | 7/2005 | Hongo et al. ..................... 435/6 |
| 2008/0223719 A1* | 9/2008 | Tam ........................ 204/403.01 |

* cited by examiner

*Primary Examiner* — J. Christopher Ball
(74) *Attorney, Agent, or Firm* — Polsinelli PC

(57) ABSTRACT

A small, portable, and inexpensive potentiostat circuit that is suitable for wide-spread electrochemical analysis is disclosed. The potentiostat may be fabricated as a stand-alone electrical component or it may be fabricated in conjunction with a Programmable System-on-Chip (SoC) to facilitate on-the-fly calibration and configuration.

24 Claims, 5 Drawing Sheets

DIGITAL POTENTIOSTAT CIRCUIT AND SYSTEM

CROSS REFERENCE TO RELATED APPLICATIONS

This application claims priority to U.S. Provisional Application No. 61/441,737 filed on Feb. 11, 2011, and entitled "Digital Potentiostat Circuit and System" which is incorporated herein by reference in its entirety.

FIELD

The present document relates to a circuit and system for electrochemical analysis, and in particular to an inexpensive digital potentiostat that provides precision and accuracy in electrochemical analysis.

BACKGROUND

Potentiostats are common tools used in electrochemical analysis. Currently, a number of companies manufacture potentiostat instruments that deliver high precision and accuracy at an equally high cost. Typically, these instruments and their accompanying software cost anywhere from $5,000 to over $20,000. As a result, these instruments are not easily accessible for wide-spread use in academic settings or other initial research studies. Although there are a number of low-cost potentiostats, such potentiostats can only deliver a low-performance capability. As such, there is a need for an easily manufactured potentiostat circuit that is inexpensive while still providing high precision and accuracy.

SUMMARY

According to one aspect, an inexpensive potentiostat circuit is provided for performing electrochemical analysis. The potentiostat circuit includes a counter electrode, a working electrode, and a reference electrode. The circuit also includes a voltage source to supply an input voltage signal and a voltage feedback component to detect a reference voltage level at the reference electrode and a working voltage level at the working electrode. The voltage feedback component also generates a feedback voltage signal based on the reference voltage and working electrode levels. A voltage inverting component supplies a working voltage signal to the working electrode. In addition, a control amplifier receives the input voltage signal and the feedback voltage signal, generates a control voltage signal based on the input voltage signal and the feedback voltage signal, and supplies the control voltage signal to the counter electrode. A current measurement component measures a current level at the working electrode and generates an output measurement signal proportional to the current level measured at the working electrode. The output measurement signal indicates a change in the working voltage level, and therefore indicates an electrochemical property of a solution in contact with the counter electrode, the working electrode, and the reference electrode. The circuit also includes an output device to receive the output measurement signal which is used to determine the electrochemical properties of the solution.

According to another aspect, a potentiostat circuit includes an electrochemical cell having a counter electrode, a working electrode, and a reference electrode. The circuit also includes a digital-to-analog converter connected to a non-inverting control amplifier input of a control amplifier and an inverting input of an inverting amplifier. The control amplifier includes the non-inverting control amplifier input, an inverting control amplifier input, and a control amplifier output, wherein the control amplifier output provides a voltage to the counter electrode to maintain a specific voltage difference between the reference electrode and the working electrode.

A voltage feedback system includes a first instrumentation amplifier having a first input, a second input, and a voltage feedback output. The first instrumentation amplifier is connected to an offset ground and the voltage feedback output is connected to the inverting input of the control amplifier and an analog-to-digital converter. The voltage feedback system removes a common-mode voltage of the reference electrode and the working electrode.

The inverting amplifier includes a number of resistors, a non-inverting input, an inverting input, and an output. The non-inverting input is connected to the offset analog ground and the inverting output is connected to the digital-to-analog converter through at least one of the resistors. The output of the inverting amplifier is connected to the working electrode and the inverting input through another of the resistors.

The circuit also includes a current measurement system having a measurement resistor and a second instrumentation amplifier. The measurement resistor is connected to the working electrode in series with the inverting operation amplifier and the second instrumentation amplifier measures a voltage difference across the measurement resistor. The output of the second instrumentation amplifier is connected to the analog-to-digital converter.

In yet another aspect, a method of using a potentiostat circuit includes generating a first voltage at a digital-to-analog converter. The first voltage is provided to a first input at an operational amplifier to amplify the difference between the first voltage and a feedback voltage. The first voltage is also provided as another input to an inverting operational amplifier to generate an inverted voltage. The amplified difference between the first voltage and a feedback voltage is provided to a counter electrode of a three-electrode cell, while the inverted voltage is provided to a working electrode of the three-electrode cell. A reference electrode voltage and a working electrode voltage are received from the three-electrode cell at a first instrumentation amplifier.

The feedback voltage is generated at the first instrumentation amplifier and the feedback voltage is provided to a second input at the operational amplifier which then provides the feedback voltage to an analog-to-digital converter. A voltage difference is measured across a resistor in series with the working electrode. The measured voltage difference is provided to a second instrumentation amplifier to determine a current received at the working electrode. A voltage signal proportional to the determined current is then provided to the analog-to-digital converter. The analog-to-digital converter generates an output measurement signal that is provided to an output device that generates output measurement data for displaying, storing, and/or printing. Electrochemical properties of a solution within the three-electrode cell are then determined based upon the displayed output measurement signal.

In other aspects, the potentiostat circuit and method are implemented in conjunction with a system-on-chip or a programmable system-on-chip, such as the Programmable System-on-Chip (PSoC®) by Cypress MicroSystems, Inc.

Additional objectives, advantages, and novel features will be set forth in the description which follows or will become apparent to those skilled in the art upon examination of the drawings and detailed description which follows.

BRIEF DESCRIPTION OF THE DRAWINGS

Corresponding reference characters indicate corresponding elements among the view of the drawings. The headings used in the figures should not be interpreted to limit the scope of the claims.

DETAILED DESCRIPTION

Figure 1:
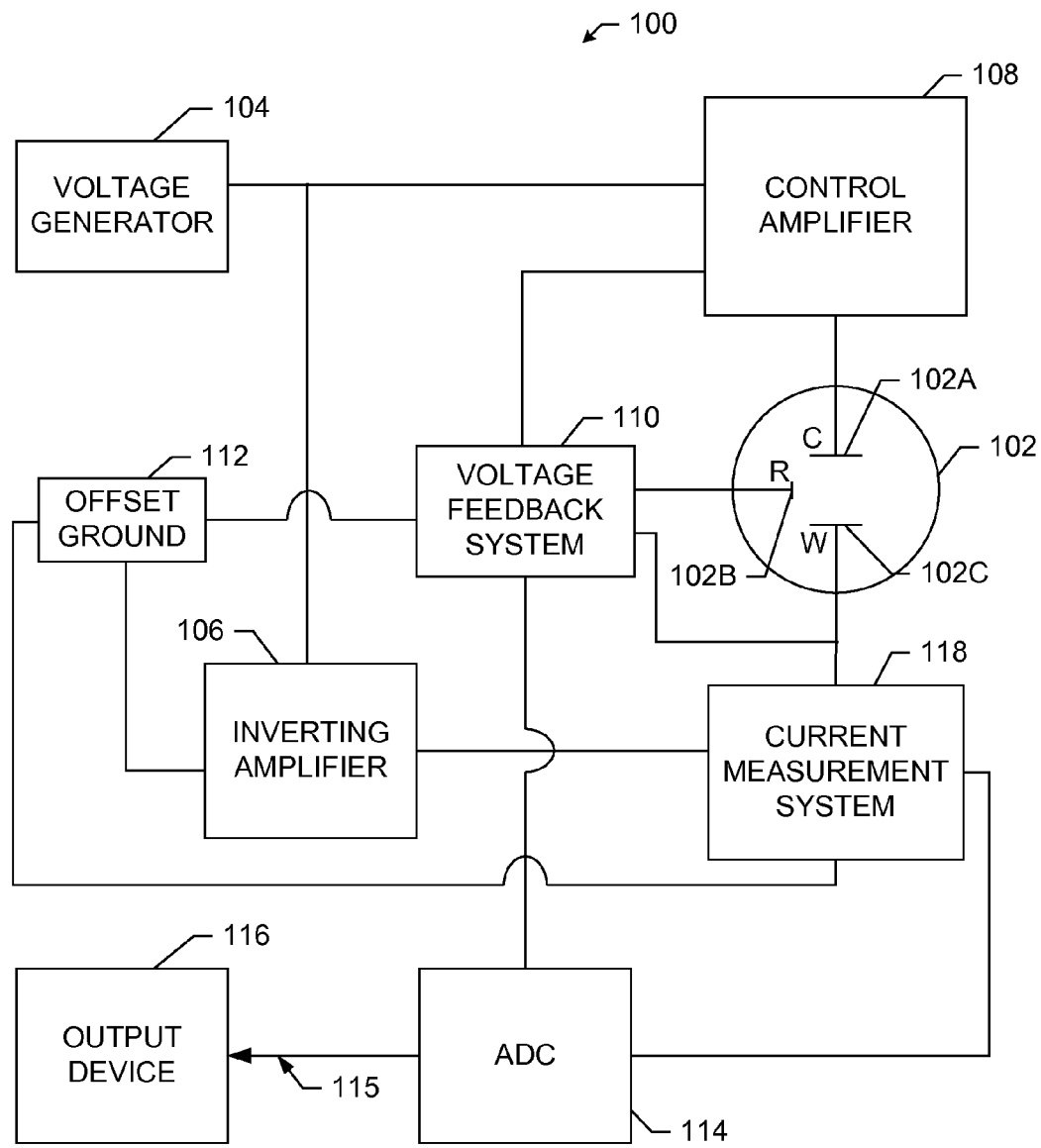
FIG. 1 is a block diagram of a potentiostat circuit.
Figure 2:
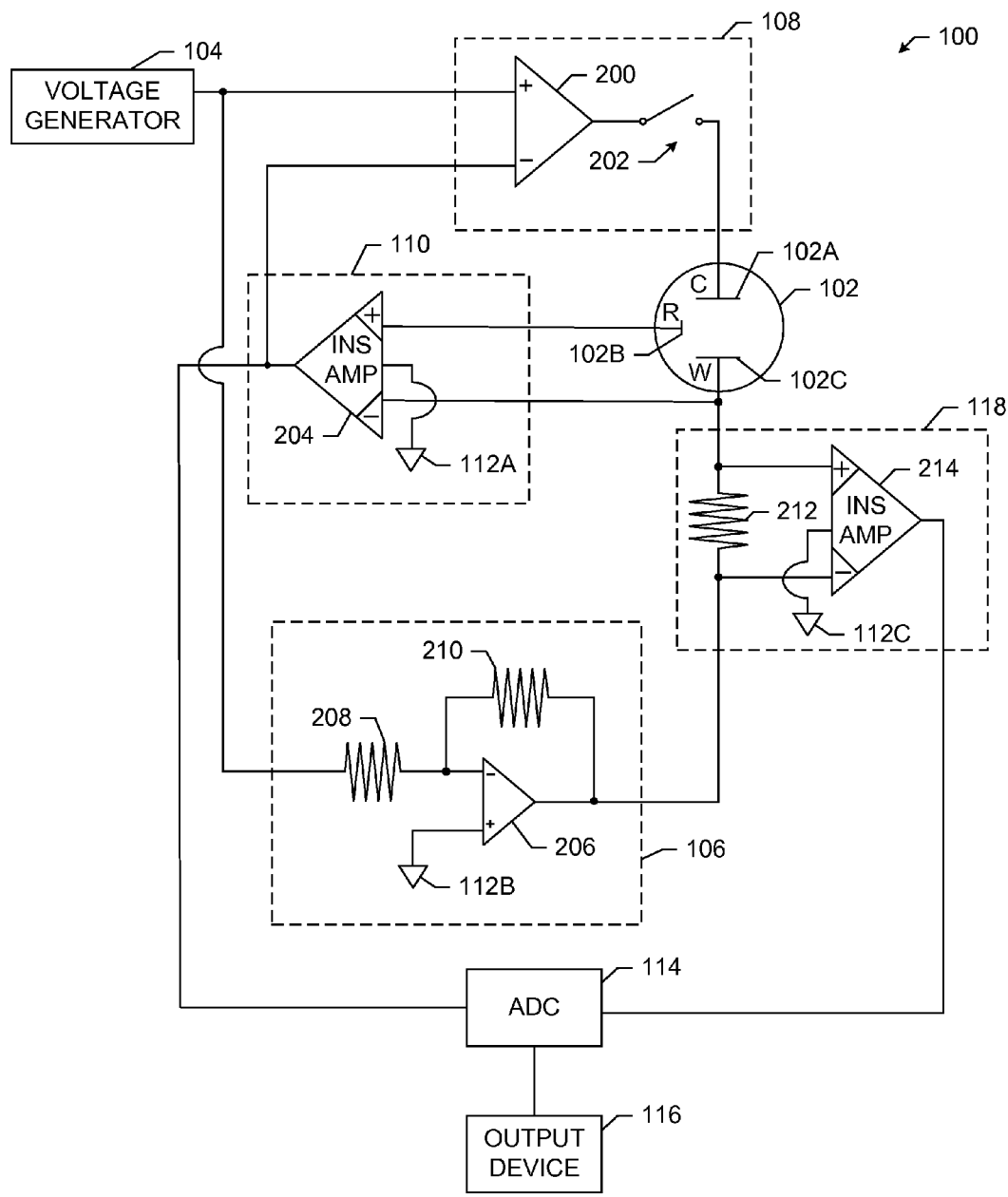
FIG. 2 is a circuit diagram of a potentiostat circuit.
Figure 3:
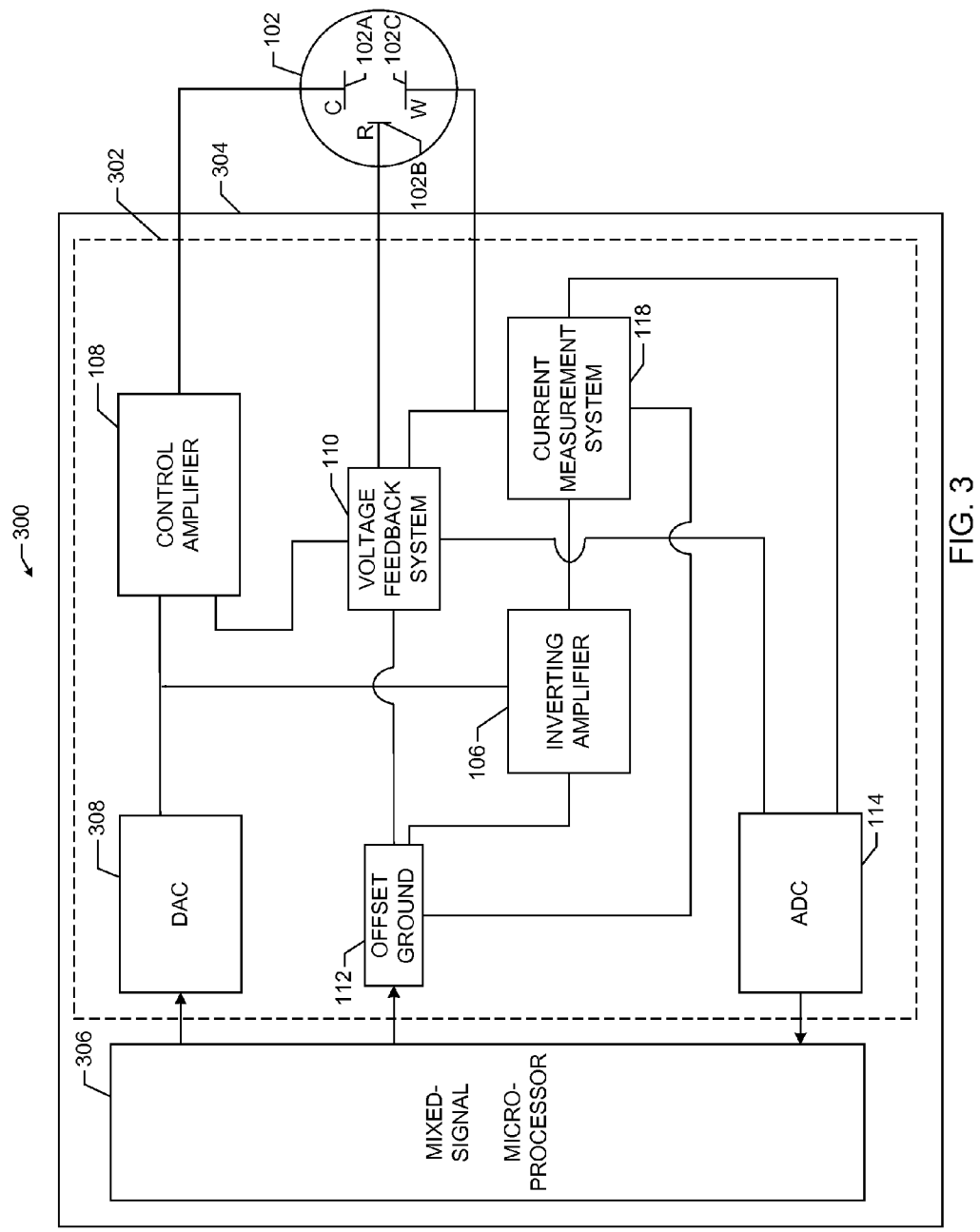
FIG. 3 is a block diagram of a potentiostat system including the potentiostat circuit shown in FIG. 1.

Referring to the drawings, an embodiment of a potentiostat circuit is illustrated and generally indicated as 100 in FIGS. 1-3. FIG. 1 is a block diagram of an embodiment of a potentiostat circuit 100 that may be used to conduct an electrochemical analysis of a solution with a three-electrode cell 102. The three-electrode cell 102 includes a counter electrode 102A, a reference electrode 102B, and a working electrode 102C.

The potentiostat circuit 100 includes a voltage generator 104 that provides analog voltages to an input of an inverting amplifier 106 and a control amplifier 108. In one embodiment, the voltage generator 104 includes a digital-to-analog converter (DAC) that provides an analog signal in response to a digital input.

The inverting amplifier 106 inverts the analog voltage received from the voltage generator 104 and provides the inverted voltage to the working electrode 102C. Another input of the inverting amplifier 106 is connected to an offset ground 112 and is held at a voltage level that is offset from ground (i.e., offset ground) 112. The offset ground 112 is an artificial ground provided by a voltage source. In one embodiment, the offset ground 112 may be provided as another voltage by the voltage generator 104.

According to one aspect, the offset ground provided to the inverting amplifier 106 is equal to one-half of a nominal power supply voltage of approximately 5V. For example, if the nominal power supply is approximately 5V, the offset ground is approximately 2.5V. In various embodiments, the nominal power supply voltage may be a nominal power supply voltage range, such as between about 4.75V and 5.25V. As the nominal 2.5V reference voltage is present at all relevant points in the system, the inverting amplifier 106 and other instrumentation amplifiers treat this as a common-mode voltage to be subtracted from the gathered measurements and/or control signals.

As explained in more detail below, according to another aspect, the potentiostat circuit 100 includes a System-on-Chip (SoC) system. In this aspect, a power supply, similar to the voltage generator 104, supplies the nominal supply voltage of approximately 5V to the SoC system and the SoC system generates the analog ground voltage of approximately 2.5V. As explained above, the analog 2.5V is present at all relevant points in the system and is treated as a common-mode voltage by the inverting amplifier 106 and other instrumentation amplifiers. The SoC system also produces a tightly regulated and temperature-independent reference voltage of approximately 1.3V that is used to operate analog-to-digital converters and the digital-to analog converters included in the potentiostat circuit 100. This temperature-independent reference voltage is also referred to as an internal bandgap reference. Accordingly, the analog voltage generated by the SoC system is constrained to operate at a range of 2.5 volts±1.3 volts, or a total range from 1.2 to 3.8 volts.

According to one aspect, the inverting amplifier 106 includes two resistors, such as an input resistor and a feedback resistor. In one example, the input resistor and the feedback resistor have resistances of 10K and 15K, respectively. The ratio of the feedback resistor to the input resistor is 1.5; therefore, the output voltage of the inverting amplifier 106 is −1.5 times the voltage applied to the control amplifier 108. As such, the inverting amplifier 106 expands the range and sensitivity of the potentiostat circuit 100. By driving the voltage for the working electrode −1.5 times the voltage supplied by the control amplifier 108, range of the voltages applied and detectable by the potentiostat circuit 100 is increased by approximately 2 volts. Therefore, the voltage range between the counter electrode 102A and the working electrode 102C is now ±4.5 volts. This expanded range is achieved without the need for additional circuitry.

The control amplifier 108 is connected to the counter electrode 102A and drives the voltage of the counter electrode 102A until the reference electrode 102B and the working electrode 102C are held at desired voltages. In one embodiment, the counter electrode 102A is driven until the difference between the voltages at the reference electrode 102B and the working electrode 102C is equal to the voltage provided by the voltage generator 104.

The control amplifier 108 also receives a voltage feedback signal from a voltage feedback system 110. The voltage feedback system 110 is connected to the reference electrode 102B and the working electrode 102C of the electrochemical cell 102. Accordingly, the control amplifier 108 provides a voltage to the counter electrode 102A that is related to the difference of the voltages between reference electrode 102B and the working electrodes 102C. As such, the voltage provided by the control amplifier 108, may be any voltage that achieves the desired difference between the voltage at the reference electrode 102B and the voltage at working electrode 102C.

In one embodiment, the voltage feedback system 110 is an instrumentation amplifier configured to determine the voltage levels of the reference electrode 102B and the working electrode 102C and generate an output that removes the common voltage shared by the electrodes 102B-C. Therefore, the output from the voltage feedback system 110 is equal to $V_{reference} - V_{working}$ ($V_{diff}$). To insure that this output is positive, the voltage feedback system 110 is also connected to an offset ground 112. In this embodiment, the offset ground 112 is the analog offset ground. $V_{diff}$ may be positive or negative and have maximum magnitude of 1.3V. Therefore, $V_{diff}$ ranges from about −1.3 to 1.3. The absolute voltages seen by the voltage feedback system 110, however, are all relative to the nominal 2.5V offset ground 112. For example, if $V_{diff}=-1.3$, the voltage feedback system 110 sees 1.2V (2.5V−1.3V=1.2V) Similarly, if $V_{diff}=1.3$, the voltage feedback system 110 3.8V (2.5V+1.3V=3.8V). Since the analog portion of the potentiostat circuit 100 system is designed around the offset ground 112, when the analog portion measures an absolute voltage of 2.5V, it interprets this voltage to be at the offset ground, i.e. 0 volts relative to the measurement being taken. Similarly, a digital-to-analog converter will produce an absolute voltage of 2.5V (analog ground) when it is instructed to generate an output of 0 volts relative to the measurement being taken.

As described above, the voltage feedback signal is representative of the difference between the voltage of the reference electrode 102B and the working electrode 102C and is provided to the control amplifier 108. In order to keep the analog voltage from the voltage generator 104 and the voltage feedback signal as close as possible, the control amplifier 108 controls the voltage level provided to the counter electrode 102A, such that the difference between the voltages of the reference electrode 102B and the working electrode 102C ($V_{reference}-V_{working}$) equals the voltage generated by the voltage generator 104.

The voltage feedback signal is also provided to an analog-to-digital convertor (ADC) 114, where an output measurement signal, as indicated by arrow 115, is generated for subsequent analysis by an output device 116. The ADC 114 has one or more inputs to receive signals from the other components of the potentiostat circuit 100. In yet another embodiment, the functionality of the ADC 114 may embodied by two or more separate but synchronized ADC components that sample the signals at the same time such that they can synchronize the voltages, signals, currents and or other data received at that same instant. The 2.5V reference voltage is used by both the analog-to-digital converters, (e.g., ADC114) and digital-to-analog converters (DAC), such as a DAC that may operate as the voltage generator 104, to make both measurements and the generated voltages absolute even though the common-mode voltage may vary. The inverting amplifier 106 and the control amplifier 108, however, are not constrained by the 2.5 volts±1.3 volts operating range. As such, the differential voltage range between the counter electrode 102A and the working electrode 102C is approximately +/−4.5V. The 0.5V difference between the nominal power supply voltage and the differential voltage range is provided as headroom for the components of the potentiostat circuit 100 to keep them operating in their linear region.

The output device 116 receives the output measurement signal from the ADC 114 and may display and/or record the signal. In various embodiments, the output device 116 is an oscilloscope, a microprocessor, or any other data acquisition device, including audio, graphical, and text-based devices. In one embodiment, the output device is in communication with and controls the voltage generator 104 to synchronize the generation and sampling of the voltages and signals.

The current measurement system 118 measures the current that is supplied to the working electrode 102C. As the voltage received at the working electrode is variable, the current is measured by determining the voltage differences across a resistor that is placed in series with the working electrode 102C.

According to one aspect, the current measurement system 118 includes an instrumentation amplifier to determine the voltage difference across the resistor. From this voltage difference, the current flowing to the working electrode 102C can be determined as a function of the voltage difference. The voltage difference as determined by the current measurement system 118 is also sent to the ADC 114. In one embodiment, the output measurement signal may be sent to another ADC 114 that is synchronized with the ADC 114.

FIG. 2 is an exemplary circuit diagram of the potentiostat circuit 100 illustrated in FIG. 1. In this embodiment, the control amplifier 108 includes an operational amplifier (op-amp) 200 that is connected to the counter electrode 102A through a controllable switch 202. The switch 202 prevents the control amplifier 108 from driving counter electrode 102A when measurements are not being taken.

In one embodiment, the switch 202 allows a user of the potentiostat circuit 100 to monitor the voltage between the reference electrode 102B and the working electrode 102C. The switch 202 may be controlled manually or automatically to measure the intrinsic voltage of a chemical solution in the electrochemical cell and to perform electrochemical titration experiments.

The op-amp 200 receives an analog voltage at the non-inverting input from the voltage generator 104 and receives another voltage at the inverting input from the voltage feedback system 110.

The voltage feedback system 110 includes an instrumentation amplifier 204 that is connected to the offset ground 112A. The instrumentation amplifier 204 receives a voltage at the non-inverting input from the reference electrode 102B and another voltage at an inverting input from the working electrode 102C. As described above, the instrumentation amplifier 204 provides a voltage feedback signal that represents the difference between the voltages of the reference electrode 102B and the working electrode 102C. When the voltages of the reference electrode 102B and the working electrode 102C are equal or the difference ($V_{diff}$) is negative, the magnitude of the voltage feedback signal may be equal to the offset ground 112A or another value relative to the nominal 2.5V offset ground. The voltage feedback system 110 also provides the voltage feedback signal to the ADC 114.

The voltage generated by the voltage generator 104 is also provided to the working electrode 102C; however, this voltage is linearly inverted with respect to the voltage at the counter electrode 102A. The inversion is provided by the inverting amplifier 106. The inverting amplifier 106 includes an op-amp 206 where the non-inverting input is connected to the offset ground 112B. The inverting input receives an analog voltage from the voltage generator 104 in series with an input resistor 208, and a feedback voltage from the op-amp 206 in series with a feedback resistor 210. The voltage output from the op-amp 206 is equal to the voltage from the voltage generator 104 times the ratio of the feedback resistor 210/input resistor 208.

In order to analyze the electrochemical properties of a solution in the three-electrode cell 102, the potentiostat circuit 100 determines the current flowing to the working electrode 102C by measuring the voltage drop across a resistor 212 at the current measurement system 118. The current measurement system 118 includes an instrumentation amplifier 214, connected to the offset ground 112C, that measures the voltage difference across the resistor 212 connected in series with the working electrode 102C. The current measurement system 118 also generates an output measurement signal and provides it to the ADC 114, where it is further provided to the output device 116.

In various embodiments, the potentiostat circuit 100 also includes a triggering signal input component (not shown) and a triggering signal output component (not shown). The triggering signal input component receives an externally generated signal to initiate the measurement gathering by the potentiostat circuit 100, such that the measurements may be synchronized with an external event. Similarly, the triggering signal output component generates a triggering signal to initiate an action at an external device to coincide with measurement gathering by the potentiostat circuit 100. In one embodiment, both triggering signal components are combined into a single component.

FIG. 3 is a block diagram of the potentiostat system 300 illustrating another embodiment of a potentiostat circuit 302. In this embodiment, the potentiostat circuit 302 is formed on a system-on-chip system (SoC) 304, such as the Programmable System-on-Chip (PSoC®) by Cypress MicroSystems, Inc. For example, the SoC 304 can be programmed to perform the functions of the various circuit components shown in FIGS. 1 and 2. In another embodiment, the potentiostat circuit 302 may be configured on a printed circuit board that is in communication with the SoC 304. The SoC 304 provides flexibility in both calibrating and configuring the potentiostat circuit 302.

The SoC 304 includes a mixed-signal microprocessor 306 configured to generate and receive both digital and analog signals, manage data acquisition and control the potentiostat functionality. The microprocessor 306 may be an 8-bit Microcontroller Unit (MCU) processor) and voltage source. In one embodiment, the microprocessor 306 may incorporate the functionalities of the voltage generator 104, the offset ground 112, and/or the ADC 114 (See FIG. 1). In this embodiment, the potentiostat circuit 302 includes a digital-to-analog convertor (DAC) 308 that converts a digital signal from the microprocessor 306 into an analog signal. The SoC 304 may also include an interface (e.g., RS-232, universal serial bus (USB), or other computer interface) configured to provide communication with a host computer (not shown) through which a user may configure the circuitry of the potentiostat circuit 302 on the SoC 304, define a protocol for an electrochemical study, and/or monitor and analyze the results of the study. The host computer may further include a graphical user interface (GUI) that enables a user to modify the structure and functionality of the potentiostat circuit as configured on the SoC 304.

In one embodiment, the microprocessor 306 is a commercially available microcontroller chip that generates voltages and signals sent to the DAC 308, generate the offset ground 112, and receive the output of ADC 114. The microprocessor 306 may also include one or more counters for synchronizing and controlling the integration time of the DAC 308 and ADC 114 to minimize the on-chip digital circuitry, thereby reducing errors and signal noise in the analog blocks.

Figure 4:
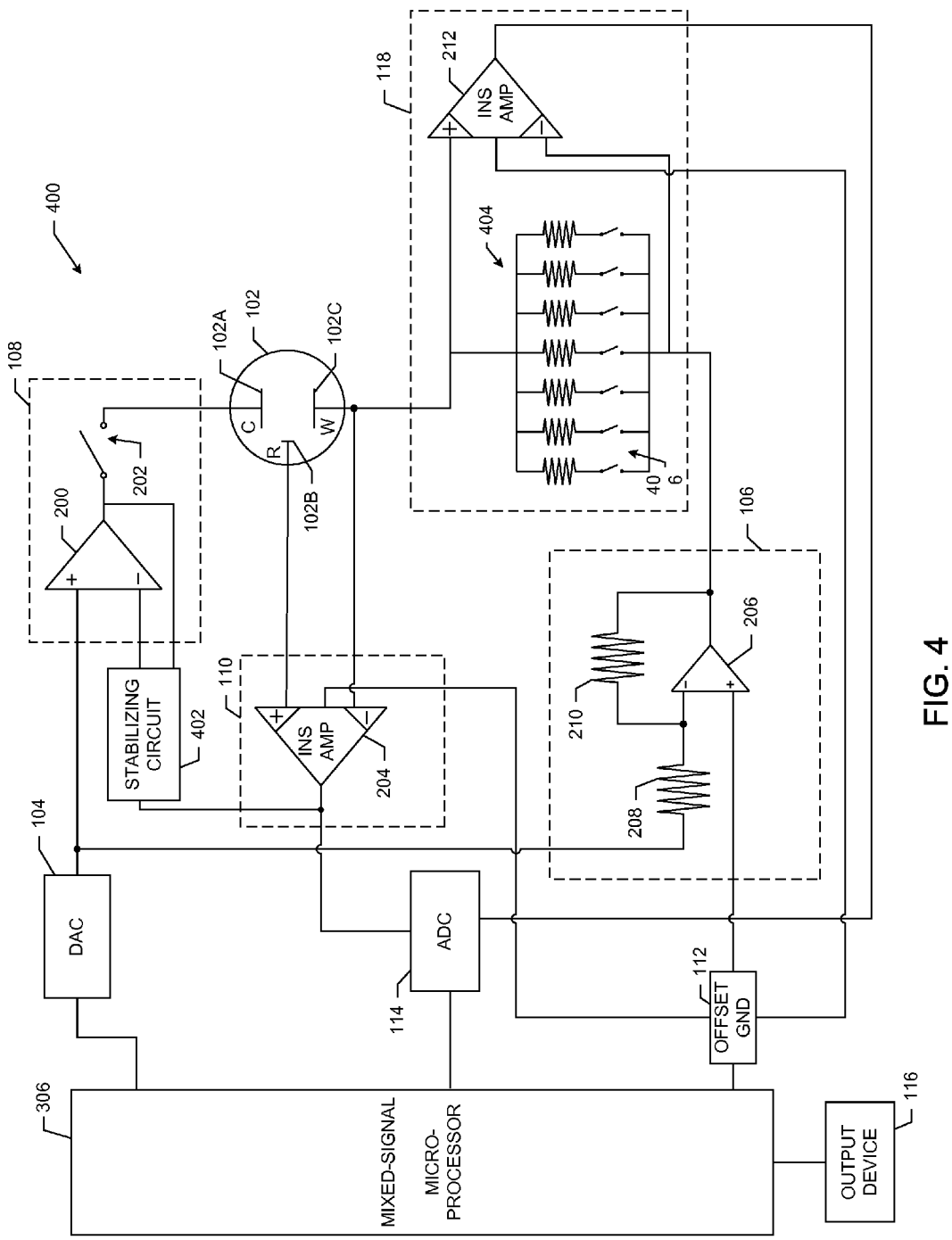
FIG. 4 is another circuit diagram of a potentiostat circuit.

FIG. 4 illustrates a circuit diagram of one embodiment of a potentiostat circuit 400. The potentiostat circuit 400 includes a stabilizing circuit 402 that prevents or dampens oscillations when the potentiostat circuit 400 is driving the cell 102 during a measurements phase. For example, the stabilizing circuit is configured to sense a voltage signal flowing through the control amplifier 108 and to provide a stable voltage feedback signal from the voltage feedback system 110 to the control amplifier. In one embodiment, the stabilizing circuit 402 stabilizes the differential output voltages from the control amplifier 108 and the voltage feedback system 110.

The potentiostat circuit 400 also includes a switch array 404 within the current measurement system 118. In one embodiment, the switch array 404 includes a bank 406 of digitally controlled analog switches to select the most appropriate resistor to sense the current flowing into the working electrode 102C. This allows the potentiostat circuit 400 to sense a wide range of currents and have the capability to automatically select the best resistor (i.e. auto-ranging). The switches of the bank 406 may be selectively closed in order to identify the voltage drop across the switch array 404 and therefore the current flowing to the working electrode 102C. In this embodiment, each of the switches includes a resistor of a different resistance to provide greater precision and accuracy. The switch array 404 and the switch 202 may be controlled by microprocessor 306.

In another embodiment, the components and functionality of the offset ground 112, the ADC 114, and the DAC 308, shown in FIGS. 3 and 4, are incorporated into the microprocessor 306. In yet another embodiment, the components and functionality of the voltage feedback system 110, the offset ground 112, the ADC 114, the current measurement system 118, and the DAC 308 are incorporated into the microprocessor 306. In these embodiments, the microprocessor 306 includes a number of input/output (I/O) pins or ports that allow the microprocessor to generate and receive digital and analog signals. In various other embodiments, the functionality of components that may be internal to the microprocessor 306, such as the offset ground 112 and the ADC 114, may be supplemented by an external component.

Figure 5:
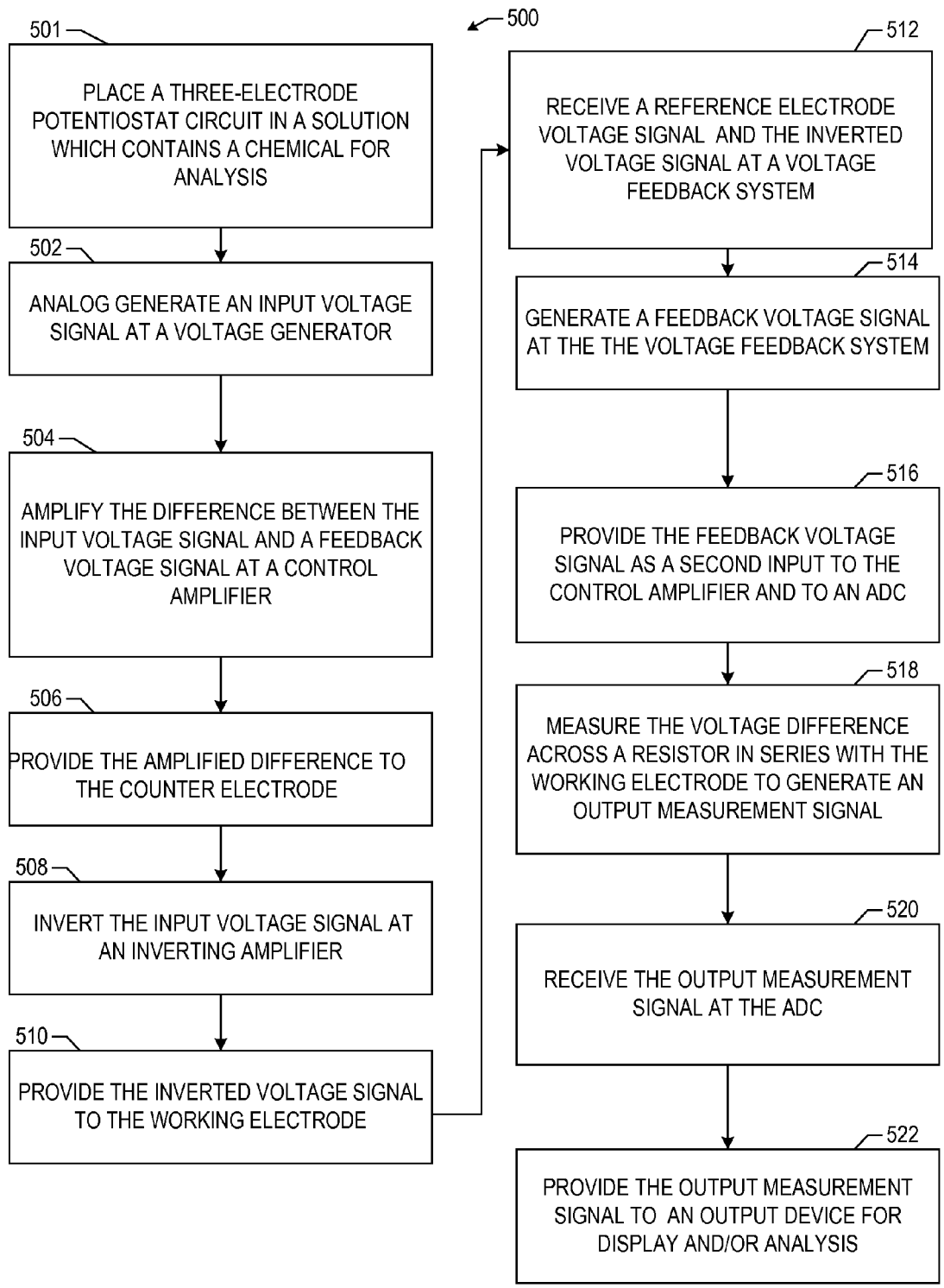
FIG. 5 is a flowchart of a method to use the potentiostat circuit to conduct electrochemical analysis.

FIG. 5 is a flowchart illustrating a method 500 of using the potentiostat circuit to conduct an electrochemical study. At 501, a three-electrode cell 102 of a potentiostat circuit is placed in a solution which contains a chemical selected to undergo electrochemical property analysis. As described above, the three-electrode cell 102 includes, for example, a counter electrode 102A, a reference electrode 102B, and a working electrode 102C. At 502, an input voltage signal is generated. In one embodiment, the input signal is generated by the voltage generator 104 (See FIGS. 1-2). In another embodiment, the input voltage is generated by the microprocessor 306 (See FIG. 3). In one embodiment, the input signal is generated as a digital signal that is converted to an analog signal by the DAC 308. In yet another embodiment, the input signal may be an analog signal generated by the microprocessor 306, thereby eliminating a need for the DAC 308.

At 504, the control amplifier 108 amplifies the difference between the input voltage signal and a feedback voltage. The amplified difference is provided to the counter electrode 102A of the three-electrode cell 102, at 506. At 508, the input voltage signal is also inverted by the inverting amplifier 106. The inverted voltage signal is provided to the working electrode 102C at 510. In one embodiment, the amplifications at 504 and 508 occur simultaneously.

A reference electrode voltage signal and the inverted voltage signal are received at the voltage feedback system 110, at 512. A feedback voltage signal is generated by the voltage feedback system 110, at 514 based upon the signals received at 512. At 516, the feedback voltage signal is provided as a second input to the control amplifier 108 and provided to the ADC 114.

The current measurement system 118 measures the voltage difference across the resistor 212 in series with the working electrode 102C and generates an output measurement signal, at 518, based on the current received at the working electrode 102C. At 520, the output measurement signal is received at the ADC 114. At 522, the output measurement signal is provided to the output device 116 where it is analyzed to determine the electrochemical properties of a solution within the three-electrode cell 102.

In one embodiment, the method 500 may further include providing a user of the potentiostat circuit 100 or a device containing the circuit, an output signal that identifies and/or quantifies an analog cell voltage and analog cell current. This analog output signal may be represented as a voltage proportional to the cell current and allows the user to view the raw analog output without it being sampled by the ADC 114.

In another embodiment, the method 500 includes receiving a trigger-in signal from the user or an external device. The trigger-in signal can be used to initiate the measurement gathering by the potentiostat circuit 100, such that the measurements may be synchronized with an external event. The trigger-in signal is received at an input of the microprocessor 306.

In yet another embodiment, the method 500 includes generating a trigger-out signal. The trigger-out signal is used to initiate an action at an external device to coincide with measurement gathering by the potentiostat circuit 100. The trigger-out signal is generated by the microprocessor 306.

It should be understood from the foregoing that, while particular embodiments have been illustrated and described, various modifications can be made thereto without departing from the spirit and scope of the invention as will be made apparent to those skilled in the art. Such changes and modifications are within the scope and teachings of this invention as defined in the claims appended hereto.

What is claimed is:

1. A potentiostat circuit comprising:
   a counter electrode;
   a working electrode;
   a reference electrode;
   a voltage source to supply an input voltage signal;
   a voltage feedback circuit to:
      detect a reference voltage level at the reference electrode and a working voltage level at the working electrode; and
      generate a feedback voltage signal based on the reference voltage and working electrode levels;
   a voltage inverting circuit to supply a working voltage signal to the working electrode;
   a control amplifier to;
      receive the input voltage signal and the feedback voltage signal;
      generate a control voltage signal based on the input voltage signal and the feedback voltage signal; and
      supply the control voltage signal to the counter electrode; and
   a current measurement circuit to:
      measure a current level at the working electrode; and
      generate an output measurement signal based on the current level, the output measurement signal indicating a change in the working voltage level.

2. The potentiostat circuit of claim 1, wherein the control amplifier further comprises:
   a non-inverting control amplifier input, an inverting control amplifier input, and a control amplifier output.

3. The potentiostat circuit of claim 2, wherein the voltage feedback circuit further comprises:
   a first instrumentation amplifier having a first input, a second input, and a voltage feedback output.

4. The potentiostat circuit of claim 3, wherein the first instrumentation amplifier is connected to an offset ground and the voltage feedback output is connected to the inverting control amplifier input of the control amplifier.

5. The potentiostat circuit of claim 3, wherein the current measurement circuit further comprises:
   a measurement resistor and a second instrumentation amplifier.

6. The potentiostat circuit of claim 5, wherein the measurement resistor is connected to the working electrode in series with the voltage inverting circuit, the second instrumentation amplifier measures a voltage difference across the measurement resistor, and an output of the second inverting amplifier is connected to an output device at a first output device input.

7. The potentiostat circuit of claim 1, wherein the voltage inverting circuit further comprises:
   a plurality of resistors, a non-inverting input, an inverting input, and an inverted output.

8. The potentiostat circuit of claim 7, wherein the non-inverting input is connected to an offset analog ground, the inverting input is connected to the voltage source through at least one resistor of the plurality of resistors, and the output of the voltage inverting circuit is connected to the working electrode and the inverting input through another resistor of the plurality of resistors.

9. The potentiostat circuit of claim 1, further comprising an output device with a first connection for receiving the output measurement signal and a second connection for operably communicating with a processor, where the voltage source and the output device are controlled by the processor.

10. The potentiostat circuit of claim 9, where the processor is a microprocessor on a mixed-signal System-on-Chip (SoC) having an analog to digital converter that receives and converts the output measurement signal to a digital output measurement signal for processing.

11. The potentiostat circuit of claim 10, where the SoC is connected to a computing device through a data bus, the computing device displaying a graphical user interface for configuring the SoC and receiving data from the potentiostat circuit.

12. A potentiostat circuit for electrochemical studies using an electrochemical cell having a counter electrode, a working electrode, and a reference electrode, the potentiostat circuit comprising:
   a digital-to-analog converter to supply an analog input voltage signal;
   a control amplifier to receive the analog input voltage signal and to provide a first voltage to the counter electrode to maintain the reference electrode at a second voltage level and the working electrode at a third voltage level;
   a voltage feedback circuit to receive a reference voltage level from the reference electrode and a working voltage level from the working electrode and outputs a common-mode voltage based on a difference between the third voltage level and the working voltage level;
   an inverting amplifier to:
      receive the analog voltage signal;
      generate an inverted analog voltage signal; and
      provide the inverted analog voltage signal to the working electrode;
   a current measurement circuit to:
      measure a current level at the working electrode; and
      generate an output measurement signal based on the current level, the output measurement signal indicating a change in the working voltage level; and
   an analog-to-digital converter to convert the output measurement signal to a digital output measurement signal for processing by an output device to indicate an electrochemical property of a solution in contact with the counter electrode, working electrode, and reference electrode.

13. The potentiostat circuit of claim 12, wherein the control amplifier further comprises:
   a non-inverting control amplifier input, an inverting control amplifier input, and a control amplifier output.

14. The potentiostat circuit of claim 13, wherein the voltage feedback circuit further comprises:
   a first instrumentation amplifier having a first input, a second input, and a voltage feedback output.

15. The potentiostat circuit of claim 14, wherein the first instrumentation amplifier is connected to an offset ground and the voltage feedback output is connected to the inverting control amplifier input of the control amplifier and the analog-to-digital converter.

16. The potentiostat circuit of claim 12, wherein the inverting amplifier further comprises:
   a plurality of resistors, a non-inverting input, an inverting input, and an output.

17. The potentiostat circuit of claim 16, wherein the non-inverting input is connected to an offset analog ground, the inverting output is connected to the digital-to-analog converter through at least one resistor of the plurality of resistors, and the output of the inverting amplifier is connected to the working electrode and the inverting input through another resistor of the plurality of resistors.

18. The potentiostat circuit of claim 12, wherein the current measurement circuit further comprises:
a measurement resistor and a second instrumentation amplifier.

19. The potentiostat circuit of claim 18, wherein the measurement resistor is connected to the working electrode in series with the inverting amplifier, the second instrumentation amplifier measures a voltage difference across the measurement resistor, and an output of the second instrumentation amplifier is connected to the analog-to-digital converter.

20. The potentiostat circuit of claim 12 where the digital-to-analog converter and the analog-to-digital converter are controlled by a processor.

21. The potentiostat circuit of claim 20, where the processor is a microprocessor on a mixed-signal System-on-Chip (SoC).

22. The potentiostat circuit of claim 21, where the SoC is connected to a computing device through a data bus, the computing device displaying a graphical user interface for configuring the SoC and receiving data from the potentiostat circuit.

23. A method of conducting electrochemical studies using a potentiostat circuit, the method comprising:
generating an input voltage signal at a voltage source;
detecting a reference voltage level of a reference electrode and a working voltage level of a working electrode at a voltage feedback circuit;
generating a feedback voltage signal based on the reference voltage and working electrode levels at the voltage feedback circuit;
providing a working voltage signal to a working electrode from a voltage inverting circuit;
receiving the input voltage signal and the feedback voltage signal at a control amplifier;
generating a control voltage signal based on the input voltage signal and the feedback voltage signal at the control amplifier;
providing the control voltage signal to the counter electrode with the control amplifier;
measuring a current level at the working electrode with a current measurement circuit;
generating an output measurement signal based on the current level with the current measurement circuit, the output measurement signal indicating a change in the working voltage level;
receiving the output measurement signal at an output device; and
determining an electrochemical property of a solution in contact with the counter electrode, the working electrode, and the reference electrode based in the output measurement signal.

24. A method of conducting electrochemical studies using a potentiostat circuit, the method comprising:
generating a first voltage at a digital-to-analog converter;
providing the first voltage to a first input at an operational amplifier to amplify a difference between the first voltage and a feedback voltage;
providing the first voltage as another input to an inverting operational amplifier to generate an inverted voltage;
providing the amplified difference between the first voltage and the feedback voltage to a counter electrode of a three-electrode cell;
providing the inverted voltage to a working electrode of the three-electrode cell;
receiving a reference electrode voltage and a working electrode voltage from the three-electrode cell at a first instrumentation amplifier;
generating the feedback voltage at the first instrumentation amplifier;
providing the feedback voltage to a second input at the operational amplifier and providing the feedback voltage to an analog-to-digital converter;
measuring a voltage difference across a resistor in series with the working electrode;
providing the measured voltage difference to a second instrumentation amplifier to determine a current level received at the working electrode as a voltage signal;
providing the voltage signal to the analog-to-digital converter and an output device as an output measurement signal; and
displaying the output measurement signal to indicate electrochemical properties of a solution within the three-electrode cell.

* * * * *